US012747011B2

(12) United States Patent
Evans et al.

(10) Patent No.: US 12,747,011 B2
(45) Date of Patent: Sep. 29, 2026

(54) OXYGEN TANK FLOTATION DEVICE

(71) Applicants: Megan Evans, Arvada, CO (US); Theresa Evans, Arvada, CO (US)

(72) Inventors: Megan Evans, Arvada, CO (US); Theresa Evans, Arvada, CO (US)

( * ) Notice: Subject to any disclaimer, the term of this patent is extended or adjusted under 35 U.S.C. 154(b) by 721 days.

(21) Appl. No.: 18/296,421

(22) Filed: Apr. 6, 2023

(65) Prior Publication Data

US 2023/0415868 A1 Dec. 28, 2023

Related U.S. Application Data

(60) Provisional application No. 63/355,715, filed on Jun. 27, 2022.

(51) Int. Cl.

*B63C 11/20* (2006.01)
*A61M 16/10* (2006.01)

(52) U.S. Cl.

CPC ....... *B63C 11/202* (2013.01); *A61M 16/1005* (2014.02); *A61M 2209/08* (2013.01)

(58) Field of Classification Search

CPC .......... A61M 16/1005; A61M 2209/08; B63C 11/202; B63C 11/20
See application file for complete search history.

(56) References Cited

U.S. PATENT DOCUMENTS

| | | | | | |
|---|---|---|---|---|---|
| 4,919,631 | A * | 4/1990 | Stafford | B63C 11/202 | 441/40 |
| 4,986,267 | A * | 1/1991 | Doss | B63C 11/202 | 128/201.27 |
| 5,299,721 | A * | 4/1994 | Cummings | B63C 11/02 | 70/164 |
| 5,546,885 | A * | 8/1996 | Porada | F17C 13/084 | 224/406 |
| 5,636,777 | A * | 6/1997 | Semeia | B63C 11/02 | 224/220 |
| 5,640,922 | A * | 6/1997 | Feldkamp | B63C 11/26 | 441/6 |
| 9,187,160 | B2 * | 11/2015 | McJunkin | B63C 11/20 | |
| 9,745,029 | B1 * | 8/2017 | Knowles | B63C 11/20 | |
| 2015/0093201 | A1 * | 4/2015 | Escano | B63C 11/202 | 405/194 |
| 2017/0050706 | A1 * | 2/2017 | Meadows | B63C 11/18 | |
| 2019/0269947 | A1 * | 9/2019 | Erickson | B62B 5/00 | |

* cited by examiner

*Primary Examiner* — Benjamin F Fiorello
(74) *Attorney, Agent, or Firm* — Brennan, Manna & Diamond, LLC

(57) ABSTRACT

The present invention relates to a novel oxygen tank flotation device. The device is designed to be used in a pool without worry of the oxygen tank tipping over into the water while exercising. The device comprises an injection-molded body preferably made from a urethane foam, in addition to a plastic superstructure. The body and superstructure have at least one continuous opening that receives an oxygen tank. The opening of the superstructure also comprises at least one ratcheting clip that secures the oxygen tank within the opening. The device further comprises a clip to secure a valve tool of the oxygen tank and a tether strap to keep the device floating near a user.

11 Claims, 9 Drawing Sheets

OXYGEN TANK FLOTATION DEVICE

CROSS-REFERENCE TO RELATED APPLICATION

The present application claims priority to, and the benefit of, U.S. Provisional Application No. 63/355,715, which was filed on Jun. 27, 2022, and is incorporated herein by reference in its entirety.

FIELD OF THE INVENTION

The present invention relates generally to the field of oxygen tank flotation devices. More specifically, the present invention relates to an improved oxygen tank flotation device that provides users with an oxygen tank that can be used in a pool. Accordingly, the present disclosure makes specific reference thereto. Nonetheless, it is to be appreciated that aspects of the present invention are also equally applicable to other like applications, devices, and methods of manufacture.

BACKGROUND

By way of background, this invention relates to improvements in oxygen flotation devices. Users who need supplemental oxygen can greatly benefit from regular exercise in a pool. However, an oxygen tank can get damaged if it is submerged in water.

This device allows people who are dependent upon supplemental oxygen to both transport on land and float their portable oxygen tank in the pool. It allows a person to wheel their oxygen tank to the edge of the pool; and then to easily secure the portable oxygen tank in the device. The user easily gets into the pool and utilizes the oxygen flotation device.

Further, the device secures to the oxygen tank so that there is no pull on the cannula, while the person is in the pool for the purpose of water therapy, medical aqua therapy, pulmonology rehabilitation, low impact water exercise, water walking and personal water recreation, etc., or any other suitable water therapy/exercise as is known in the art.

Therefore, there exists a long-felt need in the art for an oxygen tank flotation device that provides users with an oxygen tank to be used in a pool without the risk of the oxygen tank becoming submerged in the pool. There is also a long-felt need in the art for an oxygen tank flotation device that contains a cord attachment to open the tank valve when changing tanks. Further, there is a long-felt need in the art for an oxygen tank flotation device that does not interfere with the exercises or motion of the user while being used in the pool. Moreover, there is a long-felt need in the art for a device that keeps the oxygen tank from tipping over into the water while exercising. Further, there is a long-felt need in the art for an oxygen tank flotation device that comprises porous foam which allows water to drain out for easy transport of the device. Finally, there is a long-felt need in the art for an oxygen tank flotation device that allows users to easily replace new tanks in and out of the device.

The subject matter disclosed and claimed herein, in one embodiment thereof, comprises an oxygen tank flotation device. The device is designed to be used in a pool without worry of the oxygen tank tipping over into the water while exercising. The device comprises an injection-molded body preferably made from a urethane foam, in addition to a plastic superstructure. The body and superstructure have at least one continuous opening that receives an oxygen tank. The opening of the superstructure also comprises at least one ratcheting clip that secures the oxygen tank within the opening. The device further comprises a clip to secure a valve tool of the oxygen tank and a tether strap to keep the device floating near a user.

In this manner, the oxygen tank flotation device of the present invention accomplishes all of the foregoing objectives and provides users with a device that would not interfere with a user's full range of motion while exercising in the water. The device provides users with a way to easily replace new tanks in and out of the device. The device holds one "B" oxygen tank in the water without tipping or damaging the regulator.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises an oxygen tank flotation device. The device is designed to be used in a pool without worry of the oxygen tank tipping over into the water while exercising. The device comprises an injection-molded body preferably made from a urethane foam, in addition to a plastic superstructure. The body and superstructure have at least one continuous opening that receives an oxygen tank. The opening of the superstructure also comprises at least one ratcheting clip that secures the oxygen tank within the opening. The device further comprises a clip to secure a valve tool of the oxygen tank and a tether strap to keep the device floating near a user.

In one embodiment, the body component is square shaped, however the body component can be square, rectangular, triangular, circular, diamond, or oval shaped, etc., or any other suitable shape as is known in the art, depending on the needs and/or wants of a user. The size of the body component can be approximately 12-16 inches square, with a depth of 3-4 inches, depending on the needs and/or wants of a user.

In one embodiment, the body component is manufactured of foam, such that it will float and is porous which allows water to drain out. Specifically, the body component can be manufactured of high density closed-cell EVA foam, or other types of closed-cell foams, including, but not limited to, the following: Polyethylene, Cross linked Polyethylene, Polystyrene, Polyurethane, Neoprene rubber, Gym rubber, and Polypropylene foam or Styrofoam, etc., or any other suitable material as is known in the art.

In one embodiment, the body component is manufactured via vacuum molding, blow molding, or injection molding, etc., or any other suitable molding technology as is known in the art, depending on the needs and/or wants of a user.

In one embodiment, the body component comprises a shallow interior component for securing the superstructure component and a ridge or elevated perimeter component which allows the superstructure component to be positioned securely within the shallow interior component of the body component.

In one embodiment, the superstructure component is manufactured of plastic. Specifically, the superstructure component is manufactured of polypropylene; acrylic; polycarbonate, (PC); Polyethylene, (PETE, PET, PE); polyvinyl chloride (PVC); Acrylonitrile-Butadiene-Styrene, (ABS), etc., or any other suitable plastic as is known in the art.

In another embodiment, the superstructure component typically comprises four curved legs which come together to form an arched structure which suspends over the shallow interior component of the body component. Any number of curved legs can be utilized as long as an arched structure is formed which suspends over the shallow interior component of the body component.

In one embodiment, each of the four curved legs are secured to the body component via any suitable securing means as is known in the art, such as adhesives, glue, snaps, screws, bolts, etc. In one embodiment, the superstructure component is not secured to the body component but merely rests within the shallow interior component of the body component.

In one embodiment, the superstructure component and the body component comprise at least one continuous opening for receiving an oxygen tank. Generally, the device retains one "B" oxygen tank in the water, without tipping or damaging the regulator. However, any suitable size and number of oxygen tanks can be utilized as is known in the art, depending on the needs and/or wants of a user.

In one embodiment, the oxygen tank is secured within the superstructure component via a ratcheting component. The ratcheting component comprises a slider component that controls the ratcheting component and allows it to secure around the oxygen tank. The ratcheting component is engaged with the slider component, such that as the slider component moves, the ratcheting component engages the oxygen tank. Specifically, the ratcheting component is positioned around the continuous opening and contacts the slider component. The ratcheting component is positioned within a channel with the slider component, such that as the slider component is moved upward, the slider component ratchets in each slot and is prevented from coming back down and the ratcheting component secures around the oxygen tank. In one embodiment, the ratcheting component comprises a plurality of pliable teeth, or any other gripping means as is known in the art, that grip the oxygen tank. In one embodiment, the ratcheting component and the slider component are one integral piece, in another embodiment, the ratcheting component and the slider component are separate components in communication with each other or secured together via snaps, bolts, screws, adhesives, etc., or any other securing means as is known in the art.

In one embodiment, there are two ratcheting components and slider components positioned one on either side of the oxygen tank, to secure the oxygen tank within the superstructure component.

In one embodiment, the oxygen tank is secured within the superstructure component via a netting or other securing device that retains the oxygen tank within the continuous opening.

In one embodiment, the device comprises a clip which secures a valve tool or other instrument as needed. The clip is a typical clip as is known in the art and is typically secured to the superstructure component and/or the body component.

In one embodiment, the device comprises a tether strap and clip secured to the superstructure component and/or the body component to keep the device from floating away from a user. The tether strap would secure to a user's wrist or ankle, similar to a surfboard strap, and the clip would secure to the device. Alternatively, the strap can be attached to the user's swimsuit or other article of clothing. The tether strap allows a user to exercise/move in the water without worry of the device floating away, out of reach.

In one embodiment, the device comprises an additional base structure and a plurality of wheels, which can be in the form of balls, or circular wheels, etc. The wheels could be made of plastic or rubber. The wheels can be connected to a base structure or directly to the body component via any suitable securing means. The wheels can lock, swivel, float, etc. The wheels and/or additional base structure allow for the device to either be wheeled or hand carried as desired for ease in transportation.

Once the oxygen tank is secured within the device, the user then connects the cannula to their nose and ears as usual and turns on the oxygen tank. A user can then enter the pool with the oxygen tank secured on the device. The device keeps the oxygen tank afloat, out of the water, and close to the user.

Overall, the device is light-weight and simple for anyone to use. It employs long-lasting materials. It keeps the regulator part of the oxygen tank from being submerged or immersed in the water. It can be used for various sizes of small oxygen tanks. It can be prepped with the oxygen tank at any time before entering a pool or can be positioned in the device while the user is in the pool.

The invention is a floating structure adapted for use during recreational water activities. The invention is adapted for use with respiratory equipment that is required for use during recreational water activities. The invention receives and stores respiratory equipment, such as an oxygen tank, in such a manner that the respiratory equipment will float when the invention is placed in a body of water. This arrangement allows the respiratory equipment to float near the user when the user is involved in recreational water activities.

The primary object of the present invention is to provide a flotation device for individuals dependent on supplemental oxygen. This device will overcome the shortcomings of any medical, therapeutic, recreational, and pulmonary equipment currently in use or available to the public. The device serves as a flotation device for a size B portable oxygen tank. Further, the device securely holds the portable oxygen tank in place so that there is no pull on the user's cannula. The device is not a life-saving flotation device or toy. It is not for use in large bodies of deep water. In yet another embodiment, the oxygen tank flotation device comprises a plurality of indicia.

In still yet another embodiment, a method of exercising in the water along with an oxygen tank flotation device is described. The method includes the steps of providing an oxygen tank flotation device comprising an injection-molded body and a superstructure for retaining an oxygen tank. The method also comprises positioning an oxygen tank within the superstructure and securing it with a ratcheting clip, such that the oxygen tank will not tip over in the water. Further, the method comprises exercising or swimming without the oxygen tank interfering with a user's full range of motion. Finally, removing the oxygen tank from the device after use and removing the device from the pool.

Numerous benefits and advantages of this invention will become apparent to those skilled in the art to which it pertains, upon reading and understanding the following detailed specification.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
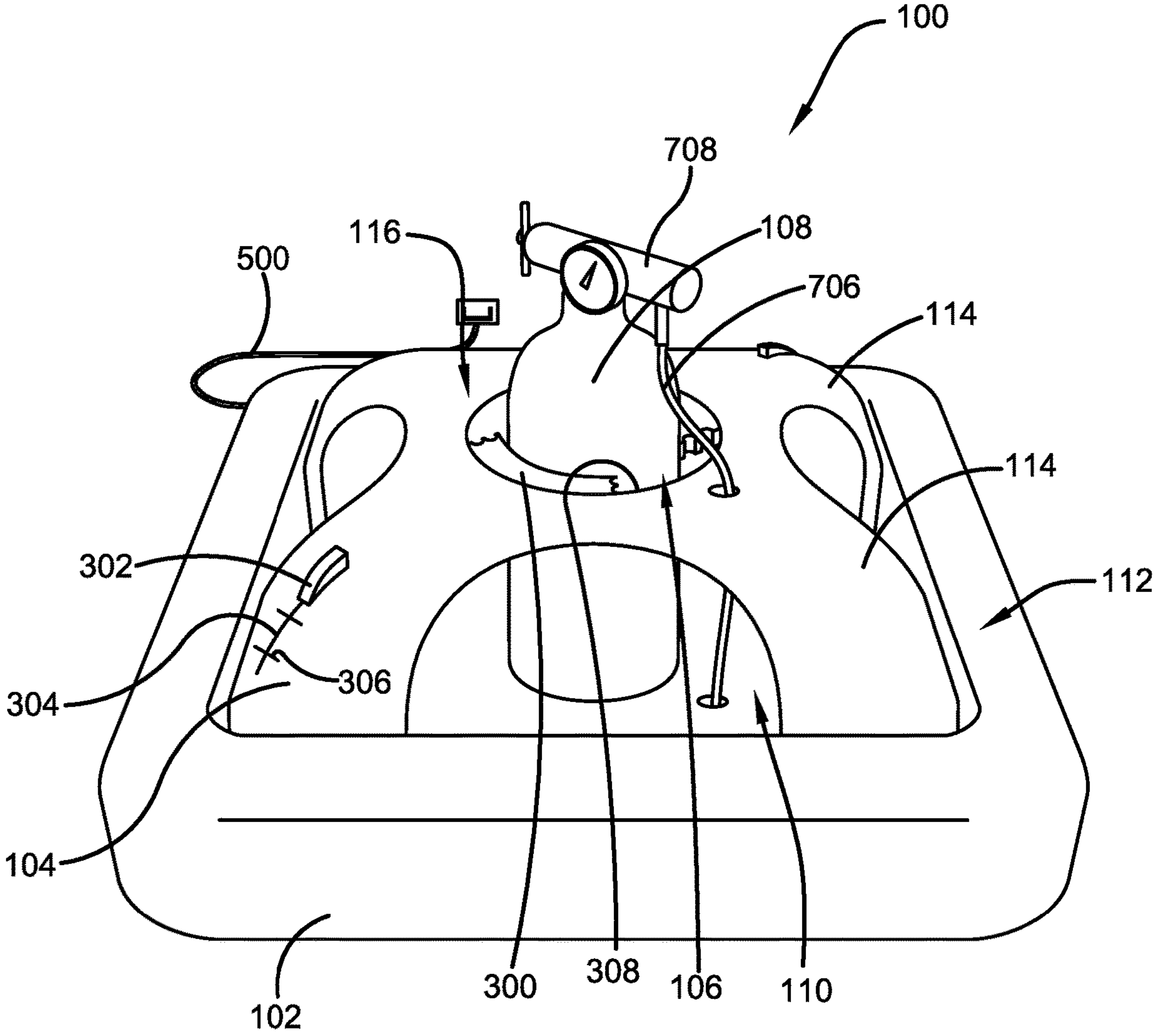
FIG. 1 illustrates a perspective view of one potential embodiment of the oxygen tank flotation device of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long-felt need in the art for an oxygen tank flotation device that provides users with an oxygen tank to be used in a pool without the risk of the oxygen tank becoming submerged in the pool. There is also a long-felt need in the art for an oxygen tank flotation device that contains a cord attachment to open the tank valve when changing tanks. Further, there is a long-felt need in the art for an oxygen tank flotation device that does not interfere with the exercises or motion of the user while being used in the pool. Moreover, there is a long-felt need in the art for a device that keeps the oxygen tank from tipping over into the water while exercising. Further, there is a long-felt need in the art for an oxygen tank flotation device that comprises porous foam which allows water to drain out for easy transport of the device. Finally, there is a long-felt need in the art for an oxygen tank flotation device that allows users to easily replace new tanks in and out of the device.

The present invention, in one exemplary embodiment, is a novel oxygen tank flotation device. The device is designed to be used in a pool without worry of the oxygen tank tipping over into the water while exercising. The device comprises an injection-molded body preferably made from a urethane foam, in addition to a plastic superstructure. The body and superstructure have at least one continuous opening that receives an oxygen tank. The opening of the superstructure also comprises at least one ratcheting clip that secures the oxygen tank within the opening. The device further comprises a clip to secure a valve tool of the oxygen tank and a tether strap to keep the device floating near a user. The present invention also includes a novel method of exercising in the water along with an oxygen tank flotation device. The method includes the steps of providing an oxygen tank flotation device comprising an injection-molded body and a superstructure for retaining an oxygen tank. The method also comprises positioning an oxygen tank within the superstructure and securing it with a ratcheting clip, such that the oxygen tank will not tip over in the water. Further, the method comprises exercising or swimming without the oxygen tank interfering with a user's full range of motion. Finally, removing the oxygen tank from the device after use and removing the device from the pool.

Referring initially to the drawings, FIG. 1 illustrates a perspective view of one embodiment of the oxygen tank flotation device 100 of the present invention. In the present embodiment, the oxygen tank flotation device 100 is an improved oxygen tank flotation device that allows a user to swim/exercise in water without risk of the oxygen tank becoming submerged or tipping over into the water. The oxygen tank flotation device 100 further comprises a body component 102, in addition to a superstructure component 104. The body component 102 and superstructure component 104 have at least one continuous opening 106 that receives an oxygen tank 108.

Typically, the body component 102 is square shaped, however the body component 102 can be square, rectangular, triangular, circular, diamond, or oval shaped, etc., or any other suitable shape as is known in the art, depending on the needs and/or wants of a user. Further, the size of the body component 102 can be approximately 12-16 inches square, with a depth of 3-4 inches, depending on the needs and/or wants of a user. Additionally, the body component 102 can be any suitable shape or size as is known in the art, depending on the needs and/or wants of a user.

Generally, the body component 102 is manufactured of porous foam, such that it will float and allows water to drain out when removed from a pool or other body of water. Specifically, the body component 102 can be manufactured of high density closed-cell EVA foam, or other types of closed-cell foams, including, but not limited to, the following: Polyethylene, Cross linked Polyethylene, Polystyrene, Polyurethane, Neoprene rubber, Gym rubber, and Polypropylene foam or Styrofoam, etc., or any other suitable material as is known in the art.

Furthermore, the body component 102 is manufactured via vacuum molding, blow molding, or injection molding, etc., or any other suitable molding technology as is known in the art, depending on the needs and/or wants of a user.

In one embodiment, the body component 102 comprises a shallow interior component 110 for securing the superstructure component 104 and a ridge or elevated perimeter component 112 which allows the superstructure component 104 to be positioned securely within the shallow interior component 110 of the body component 102. The elevated perimeter component 112 can be approximately 3-4 inches in height. Additionally, the elevated perimeter component 112 can be any suitable size and shape as is known in the art, depending on the needs and/or wants of a user.

Generally, the superstructure component 104 is manufactured of plastic. Specifically, the superstructure component 104 is manufactured of polypropylene; acrylic; polycarbonate, (PC); Polyethylene, (PETE, PET, PE); polyvinyl chloride (PVC); Acrylonitrile-Butadiene-Styrene, (ABS), etc., or any other suitable plastic as is known in the art.

In another embodiment, the superstructure component 104 typically comprises four curved legs 114 which come together to form an arched structure 116 which suspends over the shallow interior component 110 of the body component 102. Any number of curved legs 114 can be utilized as long as an arched structure 116 is formed which suspends over the shallow interior component 110 of the body component 102.

In one embodiment, each of the four curved legs 114 are secured to the body component 102 via any suitable securing means as is known in the art, such as adhesives, glue, snaps, screws, bolts, etc., depending on the needs and/or wants of a user. Furthermore, in another embodiment, the superstructure component 104 is not secured to the body component 102 but merely rests within the shallow interior component 110 of the body component 102.

Figure 2:
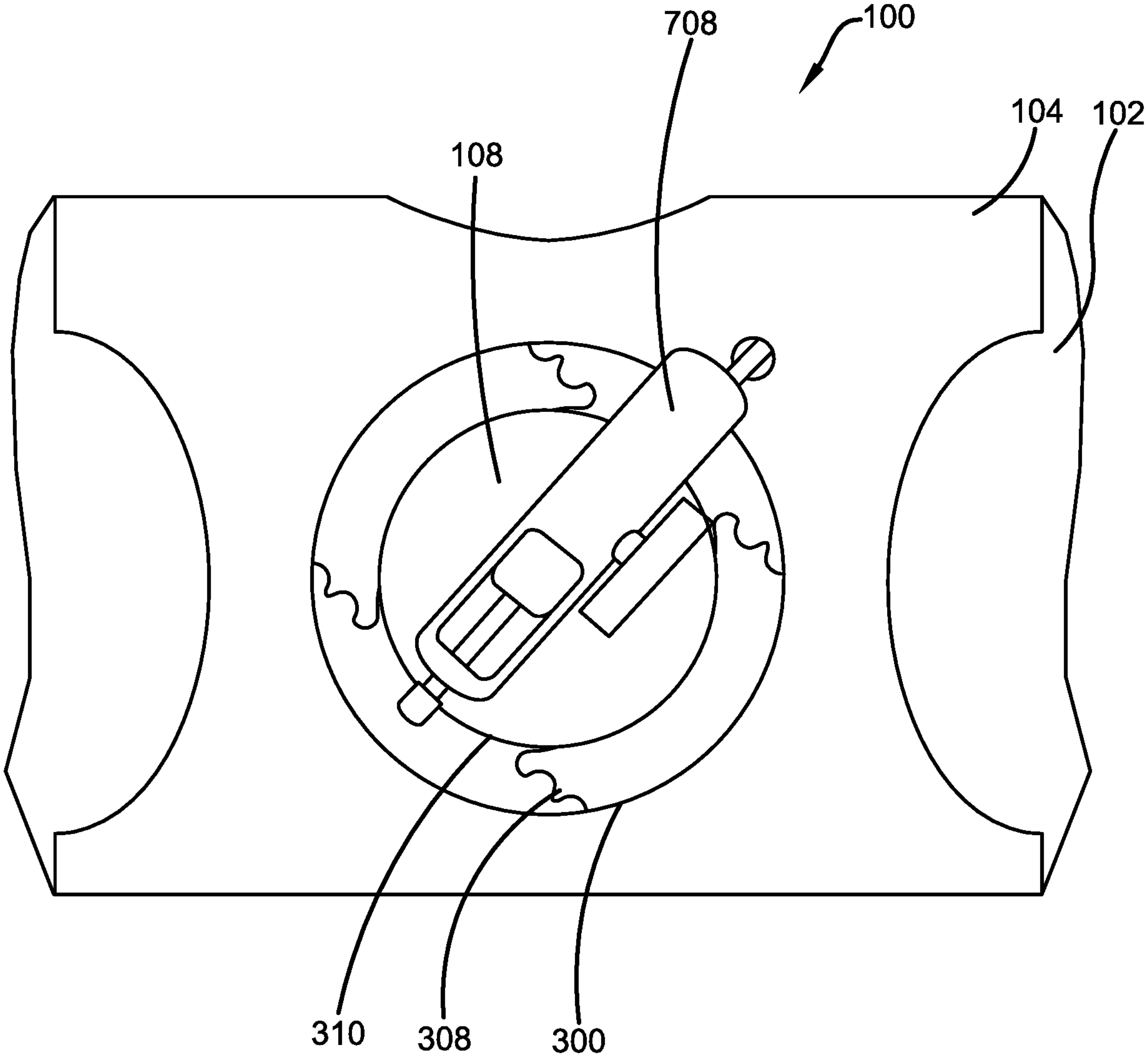
FIG. 2 illustrates a top perspective view of one potential embodiment of the oxygen tank flotation device of the present invention disclosing the oxygen valve in accordance with the disclosed architecture.

As shown in FIG. 2, the superstructure component 104 and the body component 102 comprise at least one continuous opening 106 for receiving an oxygen tank 108. Generally, the device retains one “B” oxygen tank in the water, without tipping or damaging the regulator. However, any suitable size and number of oxygen tanks 108 can be utilized as is known in the art, depending on the needs and/or wants of a user.

Figure 3:
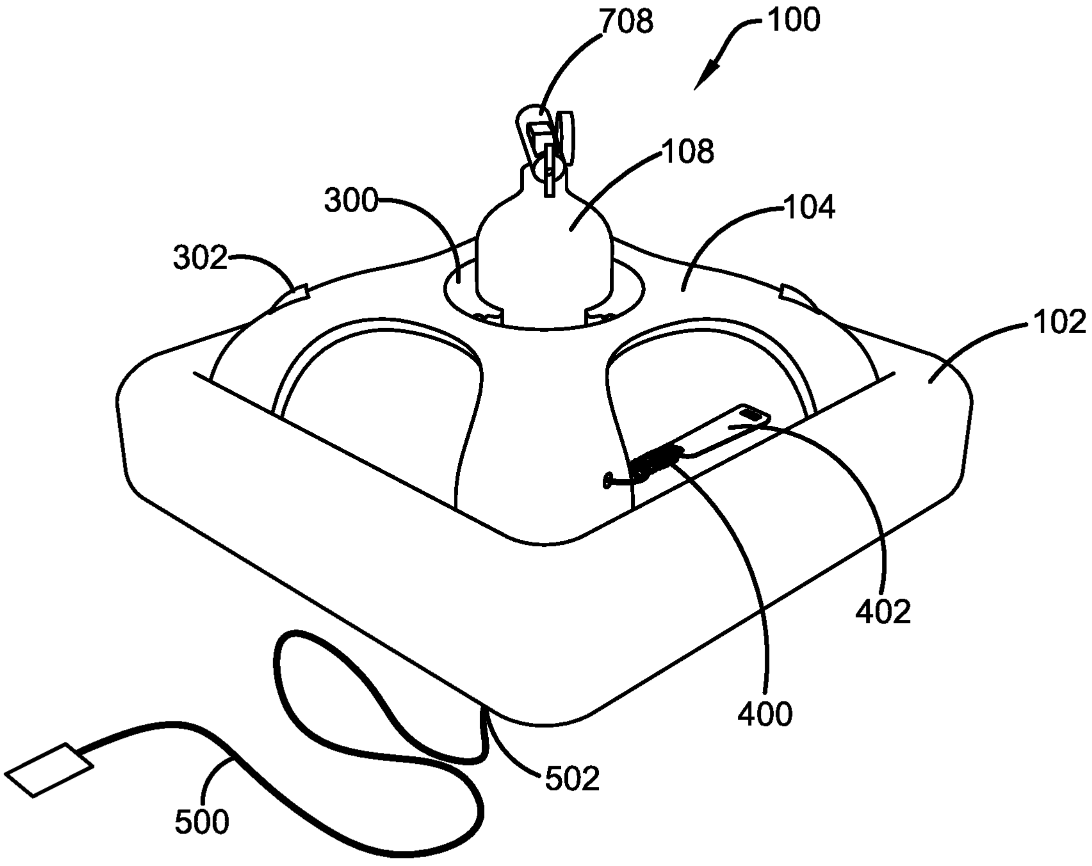
FIG. 3 illustrates a perspective view of one potential embodiment of the oxygen tank flotation device of the present invention disclosing the tether strap in accordance with the disclosed architecture.

As shown in FIGS. 2-3, the oxygen tank 108 is secured within the superstructure component 104 via a ratcheting component 300. The ratcheting component 300 comprises a slider component 302 that controls the ratcheting component 300 and allows it to secure around the oxygen tank 108. The ratcheting component 300 is engaged with the slider component 302, such that as the slider component 302 moves, the ratcheting component 300 engages the oxygen tank 108. Specifically, the ratcheting component 300 is positioned around the continuous opening 106 and contacts the slider component 302. The ratcheting component 300 is positioned within a channel 304 with the slider component 302, such that as the slider component 302 is moved upward, the slider component 302 ratchets in each slot 306 and is prevented from coming back down. As the slider component 302 moves, the ratcheting component 300 secures around the oxygen tank 108, compressing the circumference of the oxygen tank 108. In one embodiment, the ratcheting component 300 comprises a plurality of pliable teeth 308, or any other gripping means as is known in the art, that grip the oxygen tank 108. In another embodiment, the ratcheting component 300 and the slider component 302 are one integral piece, in yet another embodiment, the ratcheting component 300 and the slider component 302 are separate components in communication with each other or secured together via snaps, bolts, screws, adhesives, etc., or any other securing means as is known in the art.

In one embodiment, there are two ratcheting components 300 and slider components 302 positioned one on either side 310 of the oxygen tank 108, to secure the oxygen tank 108 within the superstructure component 104. Any number of ratcheting components 300 can be utilized as is known in the art, depending on the needs and/or wants of a user.

Figure 4:
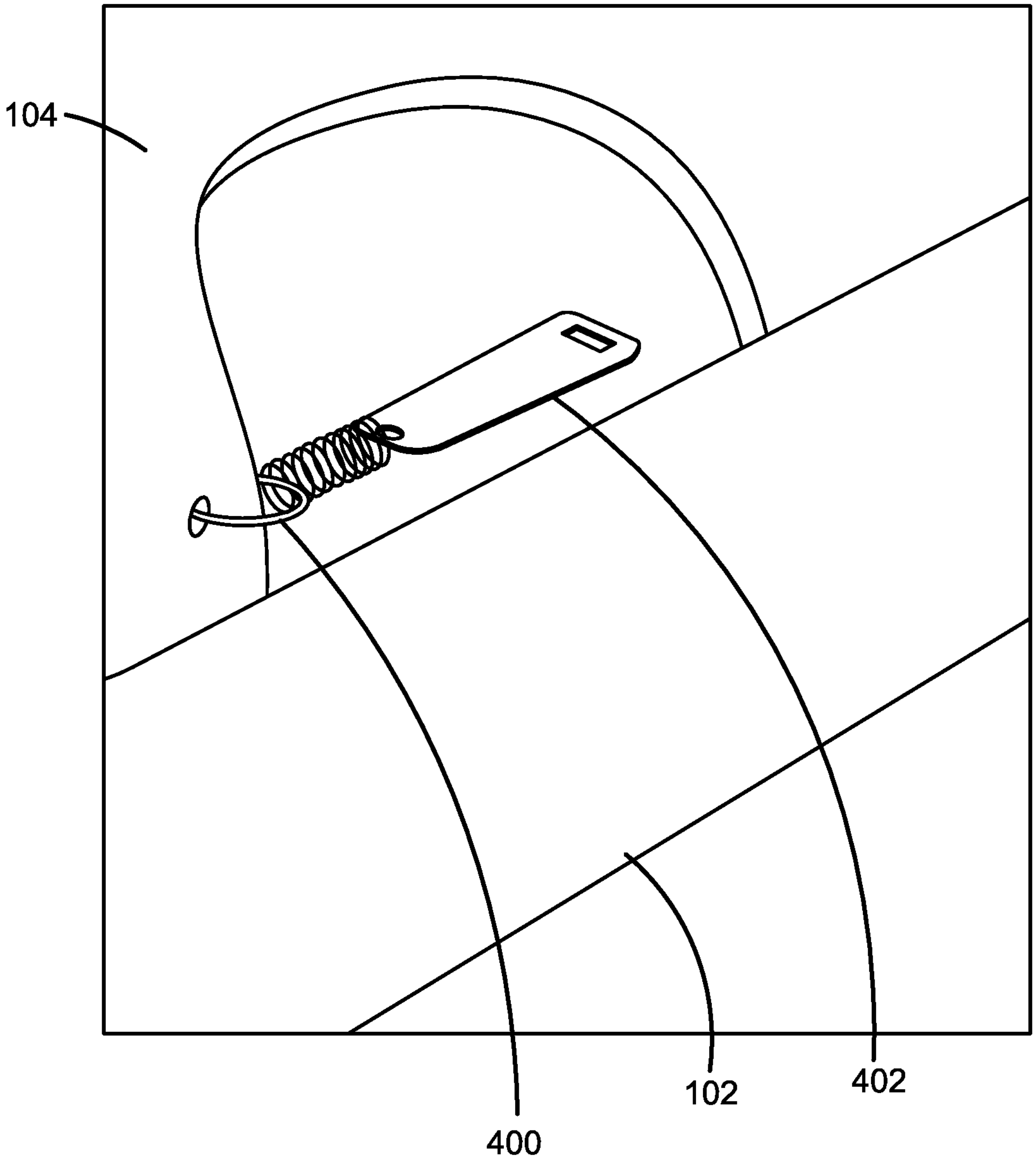
FIG. 4 illustrates a perspective view of one potential embodiment of the oxygen tank flotation device of the present invention disclosing the clip for a valve tool in accordance with the disclosed architecture.

As shown in FIG. 4, the device 100 comprises a clip 400 which secures a valve tool 402 or other instrument as needed. The clip 400 is a typical clip as is known in the art and is typically secured to the superstructure component 104 and/or the body component 102. Any suitable number of clips 400 can be utilized as is known in the art, depending on the needs and/or wants of a user.

Figure 5:
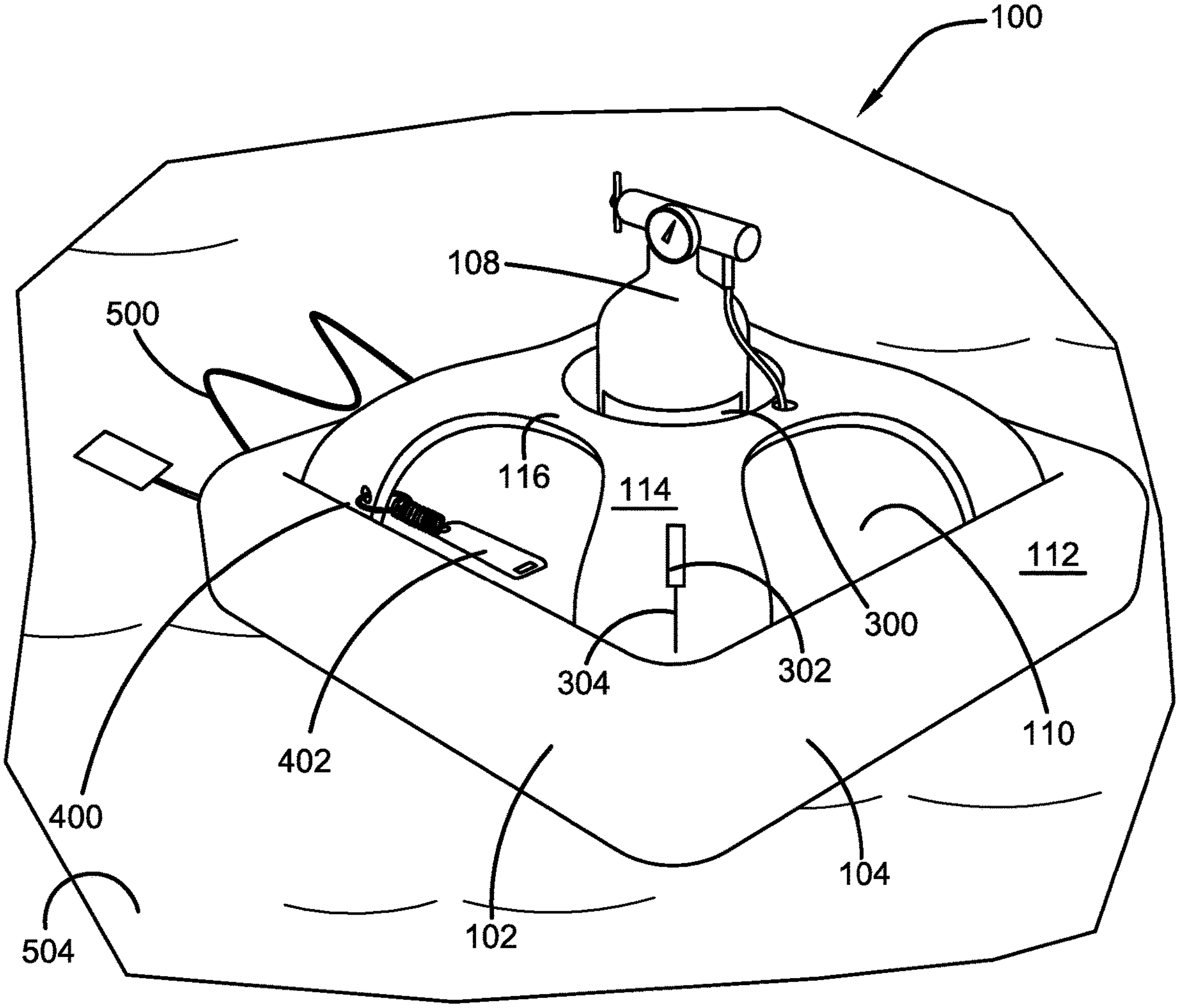
FIG. 5 illustrates a side perspective view of one potential embodiment of the oxygen tank flotation device of the present invention in use in accordance with the disclosed architecture.
Figure 6:
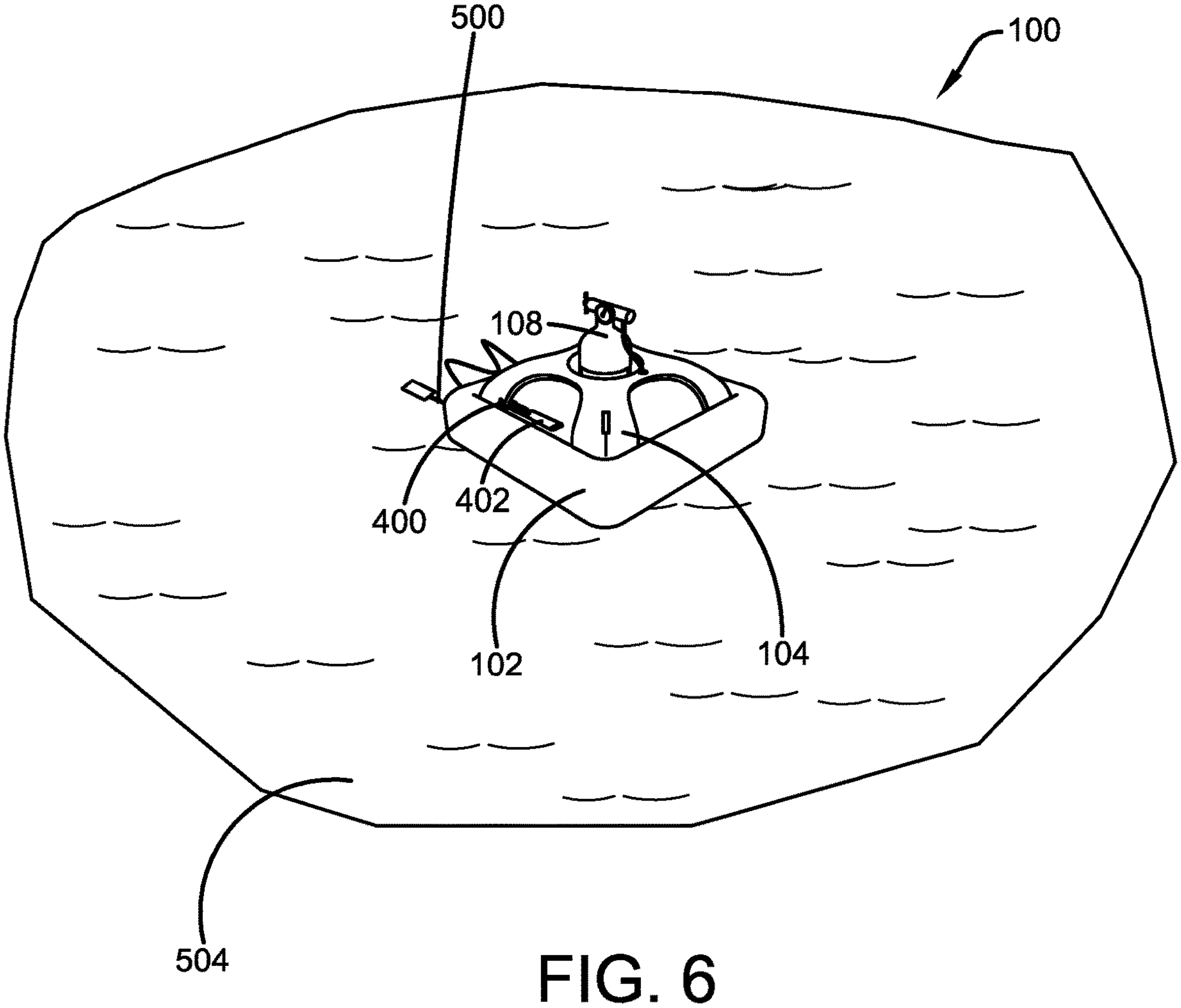
FIG. 6 illustrates a side perspective view of one embodiment of the oxygen tank flotation device of the present invention in use on a lake in accordance with the disclosed architecture.

As shown in FIGS. 5-6, the device 100 comprises a tether strap 500 and clip 502 secured to the superstructure component 104 and/or the body component 102 to keep the device 100 from floating away from a user (not shown). The tether strap 500 would secure to a user’s wrist or ankle, similar to a surfboard strap, and the clip 502 would secure to the device 100. The tether strap 500 allows a user to exercise/move in the water 504 without worry of the device 100 floating away, out of reach.

Figure 7:
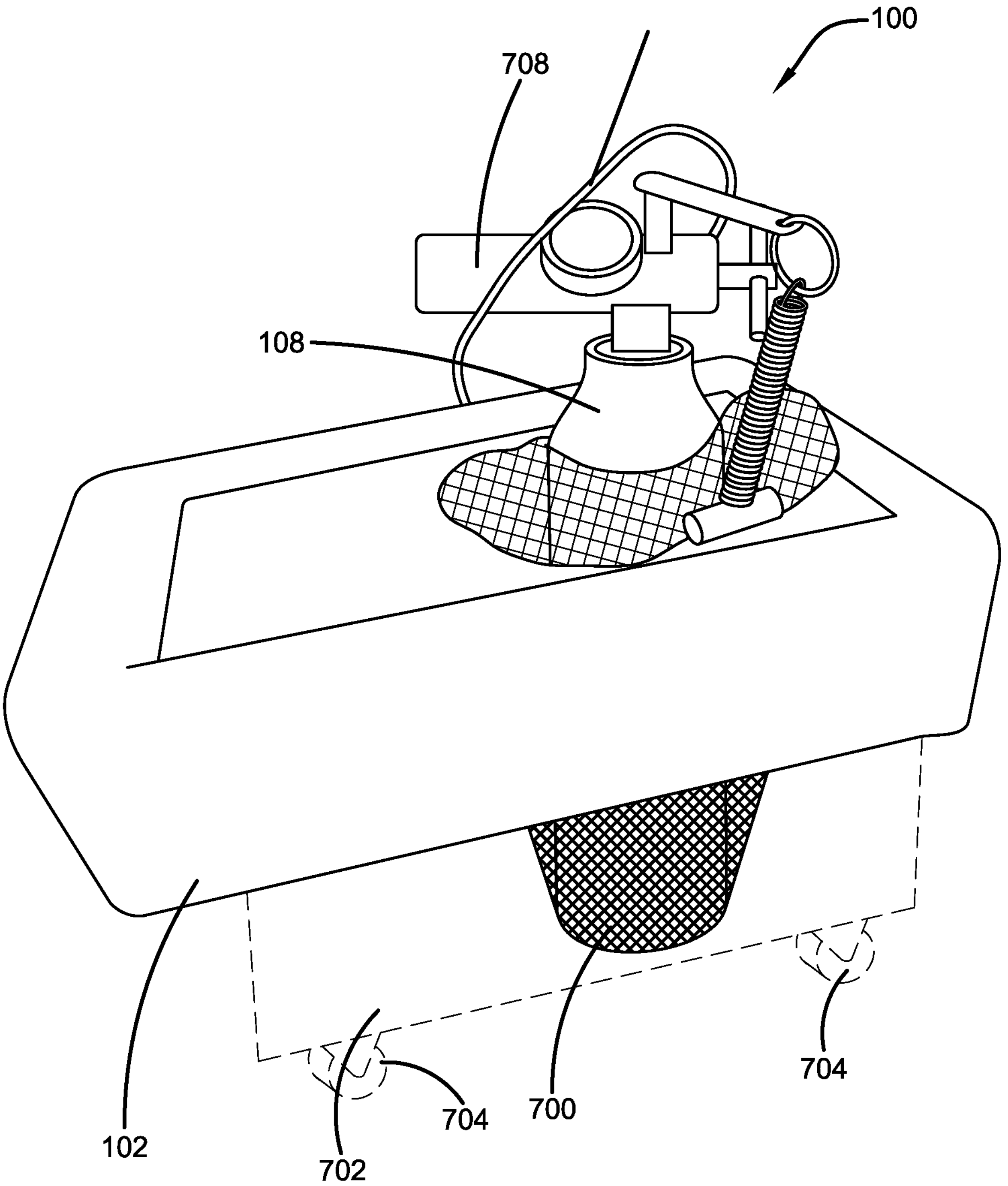
FIG. 7 illustrates a side perspective view of one potential embodiment of the oxygen tank flotation device of the present invention disclosing a net for retaining the oxygen tank within the device in accordance with the disclosed architecture.

As shown in FIG. 7, in one embodiment, the oxygen tank 108 is secured within the superstructure component 104 via a netting 700 or other securing device that retains the oxygen tank 108 within the continuous opening 106. Any suitable securing means as is known in the art can be utilized, depending on the needs and/or wants of a user.

In one embodiment, the device 100 comprises an additional base structure 702 and a plurality of wheels 704, which can be in the form of balls, or circular wheels, etc. The wheels 704 could be made of plastic or rubber. The wheels 704 can be connected to a base structure 702 or directly to the body component 102 via any suitable securing means. The wheels 704 can lock, swivel, float, etc. The wheels 704 and/or additional base structure 702 allow for the device 100 to either be wheeled or hand carried as desired for ease in transportation.

Once the oxygen tank 108 is secured within the device 100, the user then connects the cannula 706 to their nose and ears as usual and turns on the oxygen tank 108. A user can then enter the pool with the oxygen tank 108 secured on the device 100. The device 100 keeps the oxygen tank 108 afloat, out of the water 504 and close to the user.

Overall, the device 100 is light-weight and simple for anyone to use. It employs long-lasting materials. It keeps the regulator 708 part of the oxygen tank 108 from being submerged or immersed in the water 504. It can be used for various sizes of small oxygen tanks 108. It can be prepped with the oxygen tank 108 at any time before entering a pool or can be positioned in the device 100 while the user is in the pool.

The device 100 is a floating structure adapted for use during recreational water activities. The device 100 is adapted for use with respiratory equipment that is required for use during recreational water activities. The device 100 receives and stores respiratory equipment, such as an oxygen tank 108, in such a manner that the respiratory equipment will float when the device 100 is placed in a body of water 504. This arrangement allows the respiratory equipment to float near the user when the user is involved in recreational water activities.

As previously noted, the primary object of this invention is to provide a flotation device 100 for individuals dependent on supplemental oxygen. This device 100 will overcome the shortcomings of any medical, therapeutic, recreational, and pulmonary equipment currently in use or available to the public. The device 100 serves as a flotation device for a size B portable oxygen tank 108. Further, the device 100 securely holds the portable oxygen tank 108 in place so that there is no pull on the user's cannula 706. The device 100 is not a life-saving flotation device or toy. It is not for use in large bodies of deep water 504.

Generally, the oxygen tank flotation device 100 is also manufactured from a material that is water resistant and/or waterproof, or the body component 102 and/or superstructure component 104 comprises a coating that is water resistant and/or waterproof.

Figure 8A:
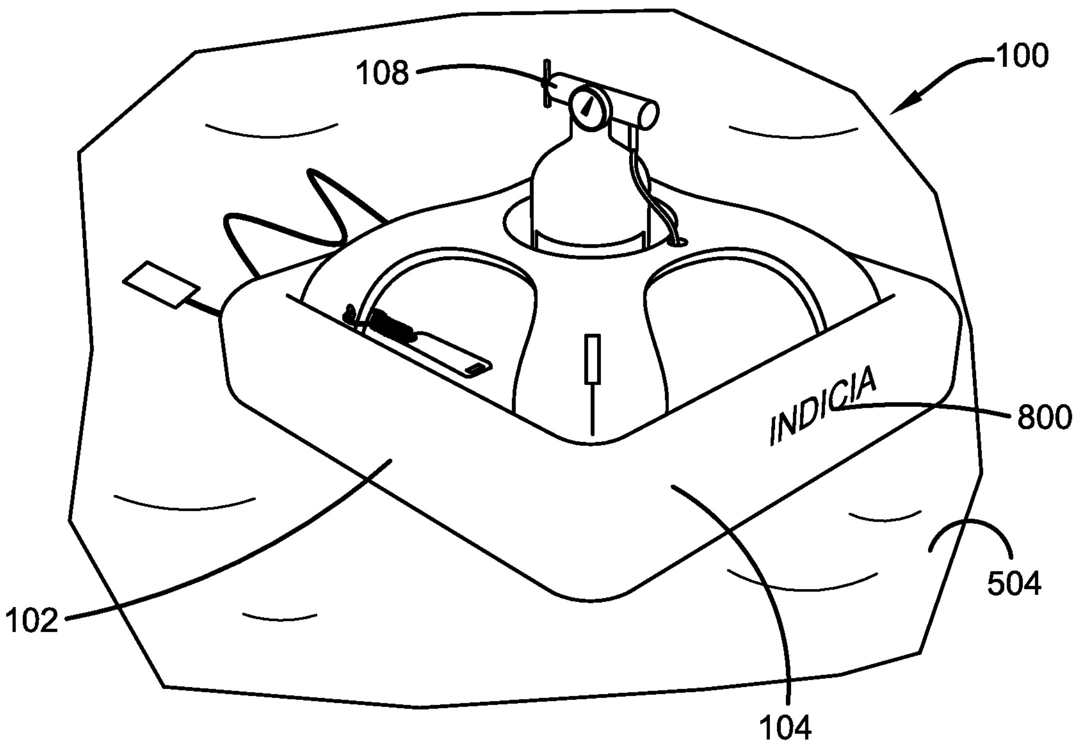
FIGS. 8A-C illustrate a perspective view of one potential embodiment of the oxygen tank flotation device of the present invention disclosing the ratcheting clips and the valve tool clip in accordance with the disclosed architecture.
Figure 8B:
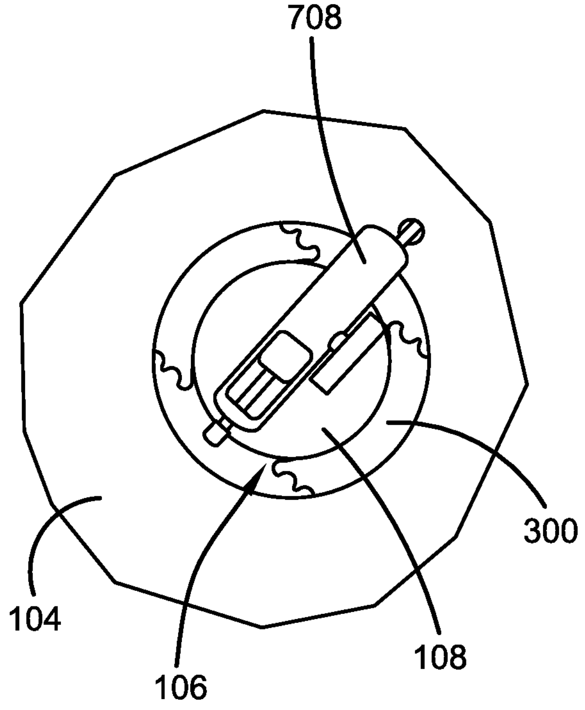
Figure 8C:
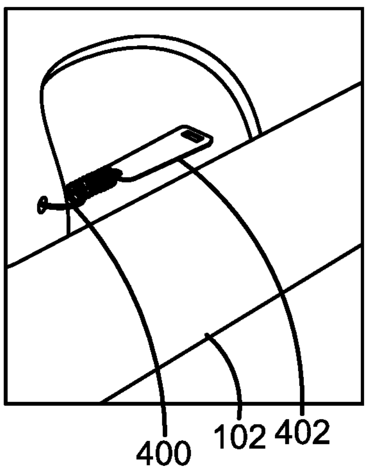

As shown in FIGS. 8A-C, the oxygen tank flotation device 100 comprises a plurality of indicia 800. The device 100 may include advertising, a trademark, or other letters, designs, or characters, printed, painted, stamped, or integrated into the body component 102 or superstructure component 104, or any other indicia 800 as is known in the art. Specifically, any suitable indicia 800 as is known in the art can be included, such as, but not limited to, patterns, logos, emblems, images, symbols, designs, letters, words, characters, animals, advertisements, brands, etc., that may or may not be oxygen tank or brand related.

Figure 9:
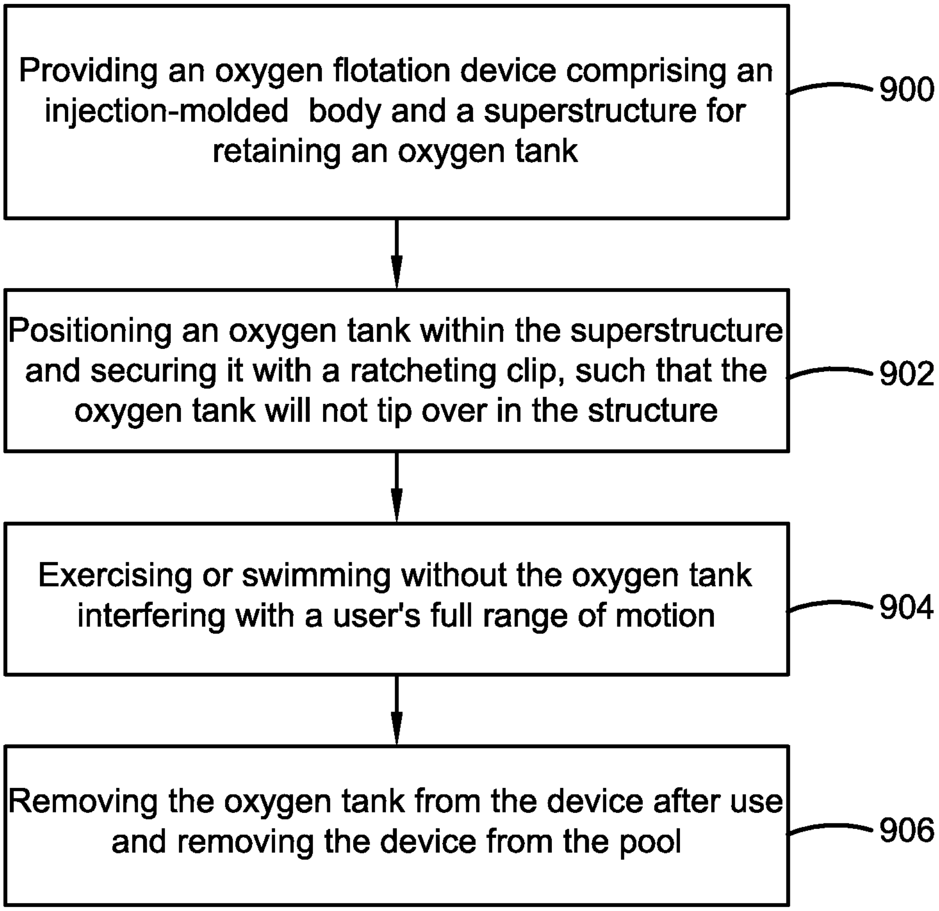
FIG. 9 illustrates a flowchart showing the method of exercising in the water along with a floating oxygen tank in accordance with the disclosed architecture.

FIG. 9 illustrates a flowchart of the method of exercising in the water along with an oxygen tank flotation device. The method includes the steps of at 900, providing an oxygen tank flotation device comprising an injection-molded body and a superstructure for retaining an oxygen tank. The method also comprises at 902, positioning an oxygen tank within the superstructure and securing it with a ratcheting clip, such that the oxygen tank will not tip over in the water. Further, the method comprises at 904, exercising or swimming without the oxygen tank interfering with a user's full range of motion. Finally, at 906, removing the oxygen tank from the device after use and removing the device from the pool.

Certain terms are used throughout the following description and claims to refer to particular features or components. As one skilled in the art will appreciate, different users may refer to the same feature or component by different names. This document does not intend to distinguish between components or features that differ in name but not structure or function. As used herein "oxygen tank flotation device", "flotation device", and "device" are interchangeable and refer to the oxygen tank flotation device 100 of the present invention.

Notwithstanding the foregoing, the oxygen tank flotation device 100 of the present invention can be of any suitable size and configuration as is known in the art without affecting the overall concept of the invention, provided that it accomplishes the above-stated objectives. One of ordinary skill in the art will appreciate that the oxygen tank flotation device 100 as shown in FIGS. 1-9 is for illustrative purposes only, and that many other sizes and shapes of the oxygen tank flotation device 100 are well within the scope of the present disclosure. Although the dimensions of the oxygen tank flotation device 100 are important design parameters for user convenience, the oxygen tank flotation device 100 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An oxygen tank flotation device that allows a user to swim or exercise in water without risk of an oxygen tank becoming submerged or tipping over into the water, the oxygen tank flotation device comprising:

a body component, wherein the body component is square shaped; and a superstructure component, wherein the body component comprises a shallow interior component and an elevated perimeter component for securing the superstructure component;

wherein the body component and the superstructure component comprise at least one continuous opening that receives an oxygen tank;

wherein once the oxygen tank is secured within the superstructure component, the user can connect a cannula to a regulator of the oxygen tank and then secure the cannula around the nose and ears of the user before turning on the oxygen tank;

wherein the superstructure component comprises four curved legs that come together to form an arched structure that suspends over the shallow interior component of the body component; and further wherein the oxygen tank flotation device keeps the oxygen tank afloat and protects the regulator of the oxygen tank from being submerged in the water.

2. The oxygen tank flotation device of claim 1, wherein the oxygen tank is secured within the superstructure component via a ratcheting component.

3. The oxygen tank flotation device of claim 2, wherein the ratcheting component comprises a slider component that controls the ratcheting component and allows the ratcheting component to secure around the oxygen tank.

4. The oxygen tank flotation device of claim 3, wherein the ratcheting component comprises a plurality of pliable teeth that grip the oxygen tank.

5. The oxygen tank flotation device of claim 4, wherein there are two ratcheting components and two slider components which are positioned one on either side of the oxygen tank to secure the oxygen tank within the superstructure component.

6. An oxygen tank flotation device that allows a user to swim or exercise in water without risk of an oxygen tank becoming submerged or tipping over into the water, the oxygen tank flotation device comprising:

a body component comprising a shallow interior component and an elevated perimeter component for securing the superstructure component; and a superstructure component comprising four curved legs which come together to form an arched structure which suspends over the shallow interior component of the body component;

wherein the body component and the superstructure component comprise at least one continuous opening that receives an oxygen tank;

wherein the oxygen tank is secured within the superstructure component via a ratcheting component and a slider component that allows the ratcheting component to secure around the oxygen tank;

wherein there are two ratcheting components and two slider components which are positioned one on either side of the oxygen tank to secure the oxygen tank within the superstructure component; and further wherein once the oxygen tank is secured within the superstructure component, a user can connect a cannula to a regulator of the oxygen tank and then secure the cannula around their nose and ears and turn on the oxygen tank.

7. The oxygen tank flotation device of claim 6, wherein the ratcheting component comprises a plurality of pliable teeth that grip the oxygen tank.

8. The oxygen tank flotation device of claim 6 further comprising a clip which secures a valve tool.

9. The oxygen tank flotation device of claim 6 further comprising a tether strap and a clip secured to the superstructure component or the body component.

10. The oxygen tank flotation device of claim 6 further comprising a plurality of indicia.

11. The oxygen tank flotation device of claim 6 further comprising a base structure and a plurality of wheels for transportation.

* * * * *